(12) United States Patent
Mor et al.

(10) Patent No.: US 7,927,833 B2
(45) Date of Patent: Apr. 19, 2011

(54) COMPOSITION AND METHOD FOR ENHANCING IMMUNE RESPONSE

(75) Inventors: Tsafrir S. Mor, Tempe, AZ (US);
Nobuyuki Matoba, Tempe, AZ (US);
Charles J. Arntzen, Superstition Mountain, AZ (US)

(73) Assignee: Arizona Board of Regents, Acting For and on Behalf of Arizona State University, Tempe, AZ (US)

( * ) Notice: Subject to any disclaimer, the term of this patent is extended or adjusted under 35 U.S.C. 154(b) by 109 days.

(21) Appl. No.: 12/211,544

(22) Filed: Sep. 16, 2008

(65) Prior Publication Data
US 2009/0117145 A1    May 7, 2009

Related U.S. Application Data

(62) Division of application No. 10/506,796, filed as application No. PCT/US03/07073 on Mar. 6, 2003, now Pat. No. 7,438,914.

(60) Provisional application No. 60/362,247, filed on Mar. 6, 2002.

(51) Int. Cl.
*C12N 15/00* (2006.01)
*A61K 39/395* (2006.01)

(52) U.S. Cl. ............... 435/69.1; 424/187.1; 424/236.1; 435/320.1

(58) Field of Classification Search .................. None
See application file for complete search history.

(56) References Cited

U.S. PATENT DOCUMENTS

| | | | | |
|---|---|---|---|---|
| 5,750,332 A | * | 5/1998 | Robey et al. | 435/5 |
| 6,258,782 B1 | | 7/2001 | Barney et al. | 514/13 |
| 6,271,198 B1 | | 8/2001 | Braisted et al. | 514/2 |

OTHER PUBLICATIONS

Haddad et al. Eukaryotic cell 2002, vol. 1, No. 4, pp. 583-593.*
Sirrangapatnam et al. Am J. Physiology 2007, vol. 293, C558-C565.*
Backstrom et al., "Characterization of an internal permissive site in the cholera toxin B-subunit and insertion of epitopes from human immunodeficiency virus-I, hepatitis B virus and enterotoxigenic *Escherichia coli.," Gene*, 165:163-171, 1995.
Backstrom et al., "Insertion of a HIV-1 neutralizing epitope in a surface-exposed internal region of the cholera-B subunit," *Gene*, 149:211-217, 1994.
Coeffier et al., Antigenicity and immunogenicity of the HIV-1 gp41 epitope ELDKWA inserted into permissive sites of the MalE protein, *Vaccine*, 19:684-693, 2001.
Durrani et al. "Intranasal immunization with a plant virus expressing a peptide from HIV-1 gp41 stimulates better mucosal and systemic HIV-1-specific IgA and IgG than oral immunization," *J. Immunol. Methods*, 93:93-103, 1998.
George-Chandy et al., "Cholera toxin B subunit as a carrier molecule promotes antigen presentation and increases CD40 and CD86 expression on antigen-presenting cells," *Infection and Immunity*, 69(9):5716-5725, 2001.
Office Communication, issued in U.S. Appl. No. 10/506,796, dated Mar. 26, 2007.
Office Communication, issued in U.S. Appl. No. 10/506,796, dated Dec. 11, 2007.

* cited by examiner

*Primary Examiner* — Bao Li
(74) *Attorney, Agent, or Firm* — Fulbright & Jaworski L.L.P.

(57) ABSTRACT

A composition and method for enhancing immune response in a living organism is disclosed. In particular, the present disclosure provides an adjuvant peptide for use in raising an immune response to an antigen. The adjuvant peptide is selected from a group of peptides with an HIV-related sequence. Additionally, the adjuvant peptide can comprise a fusion-protein that acts as a mucosal adjuvant. The adjuvant peptide can be transformed into one or more living cells, such that the mucosal adjuvant can be produced in living cells and then administered by systemic, mucosal or epidermal delivery.

5 Claims, 11 Drawing Sheets

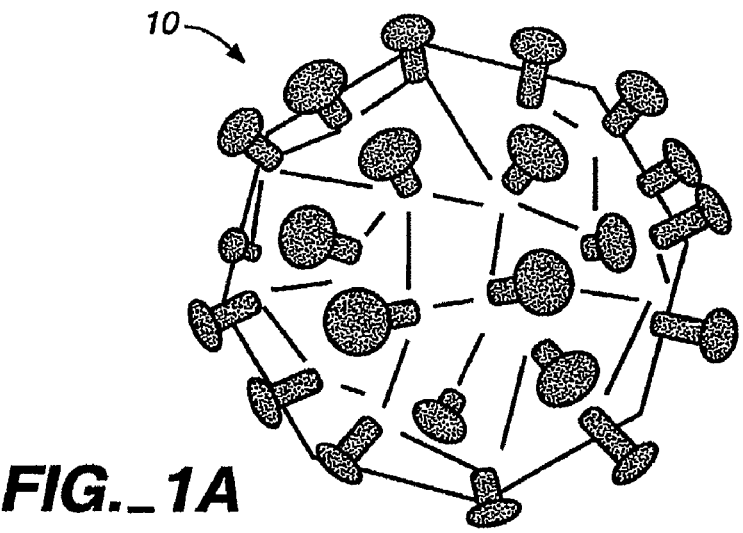
FIG._1A
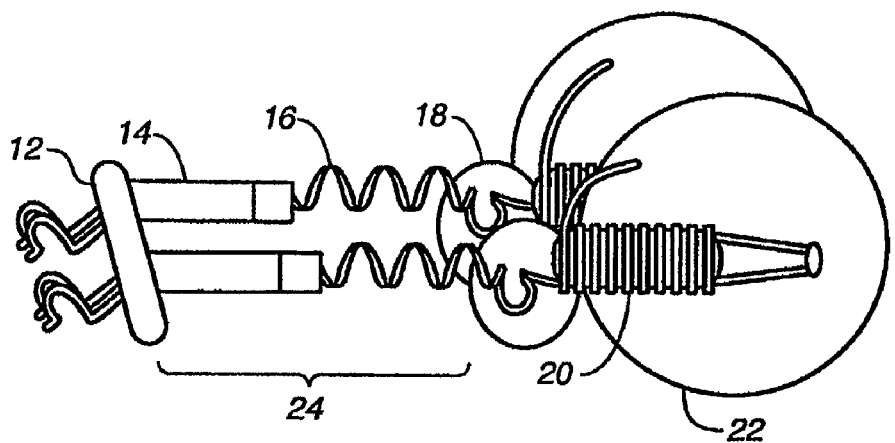
FIG._1B
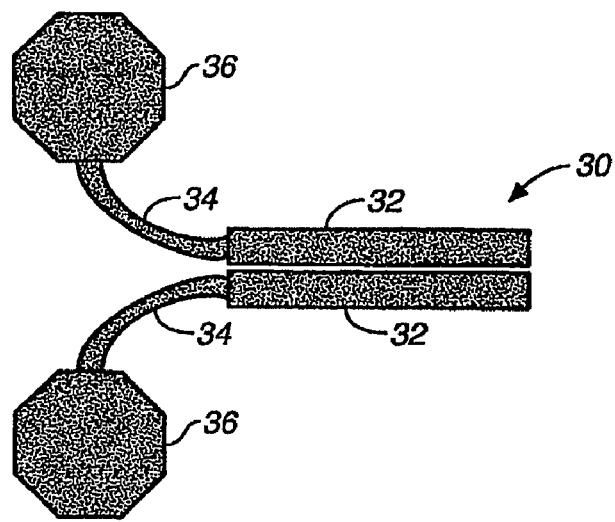
FIG._2

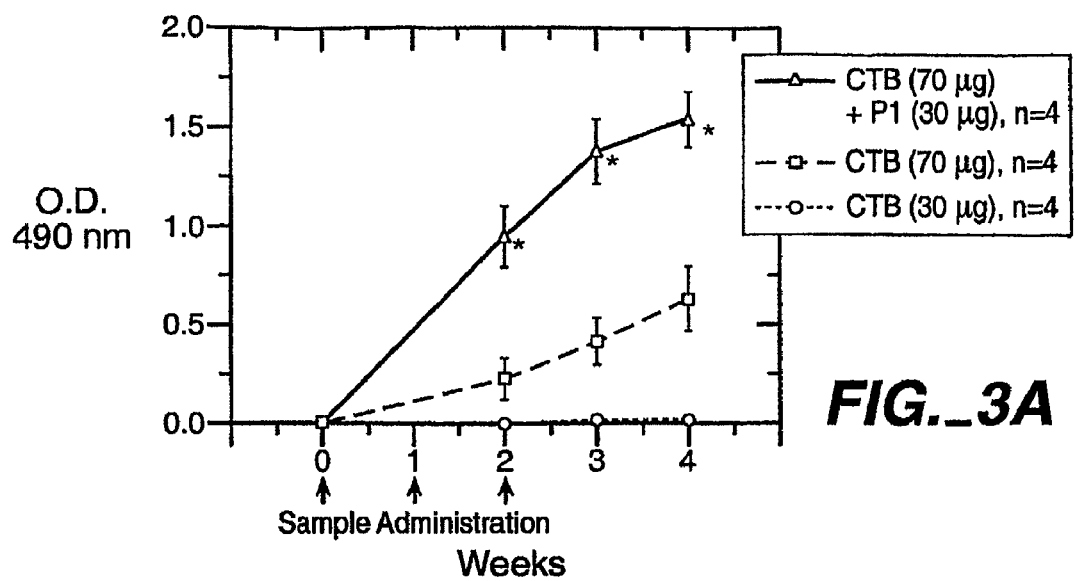
FIG._3A
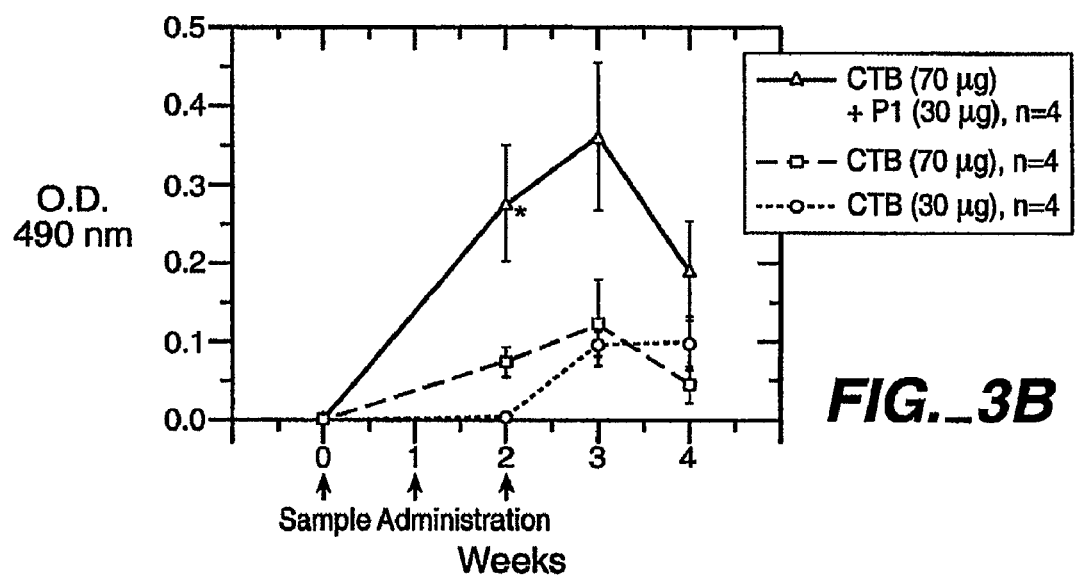
FIG._3B
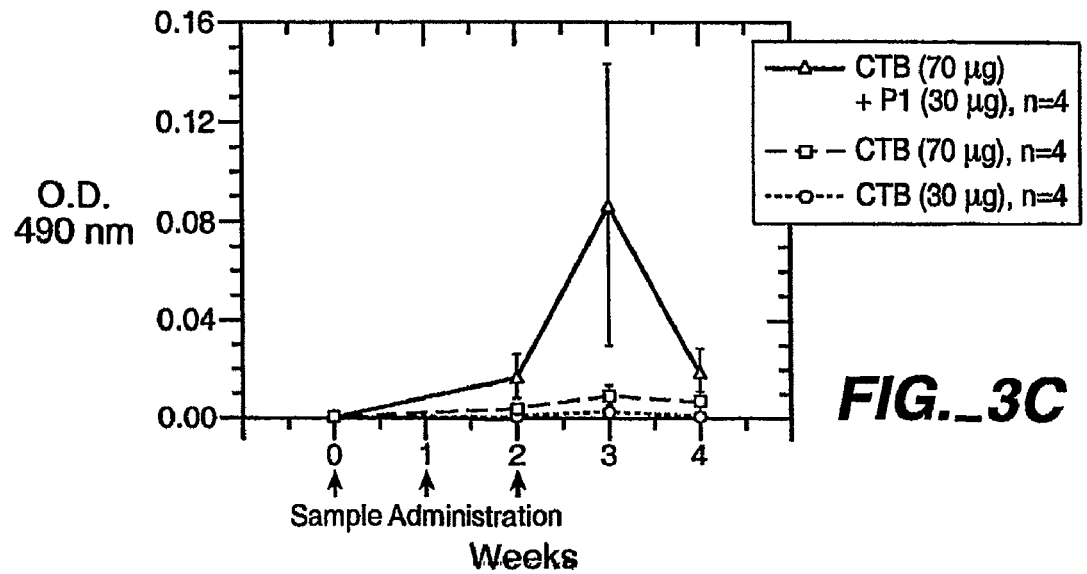
FIG._3C

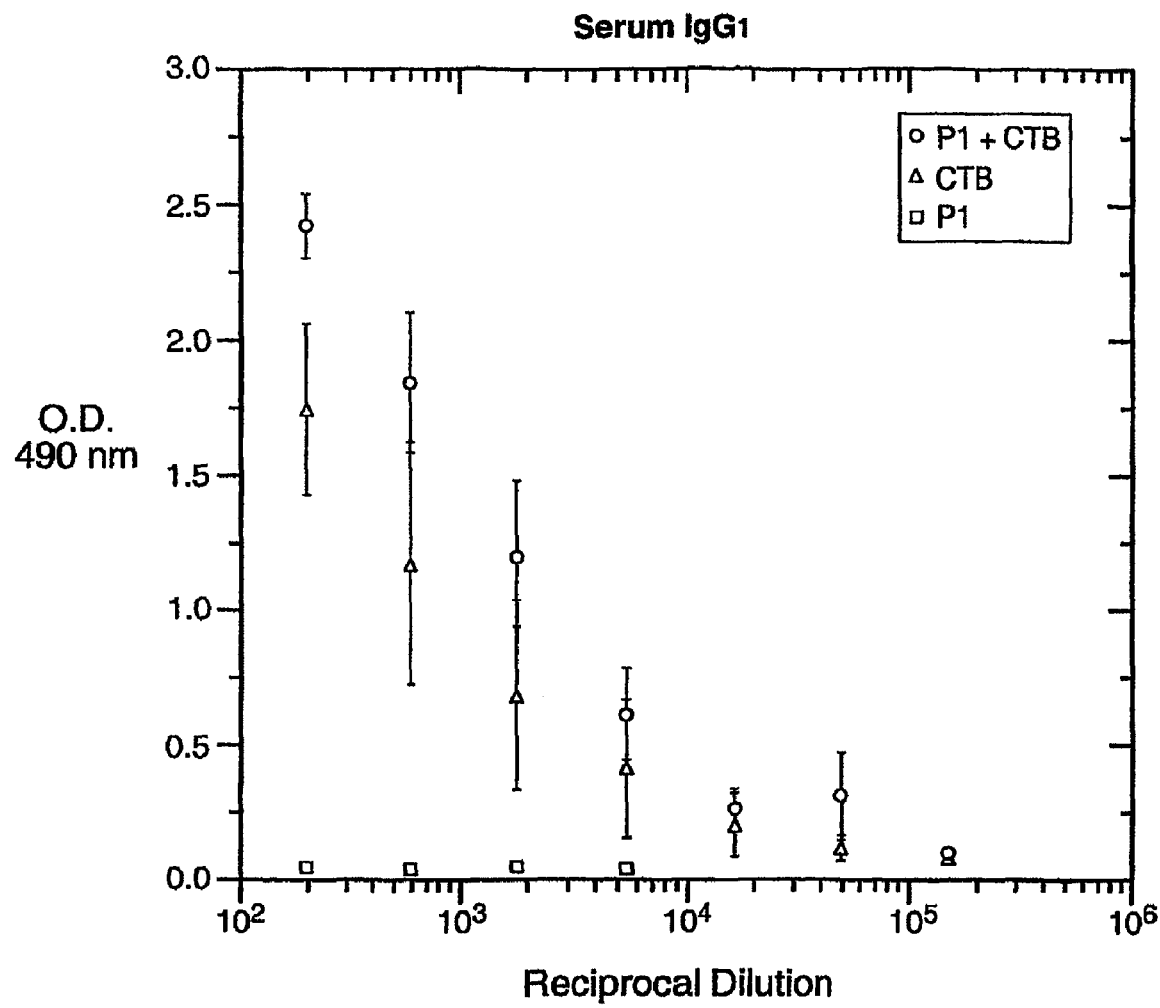
FIG._5

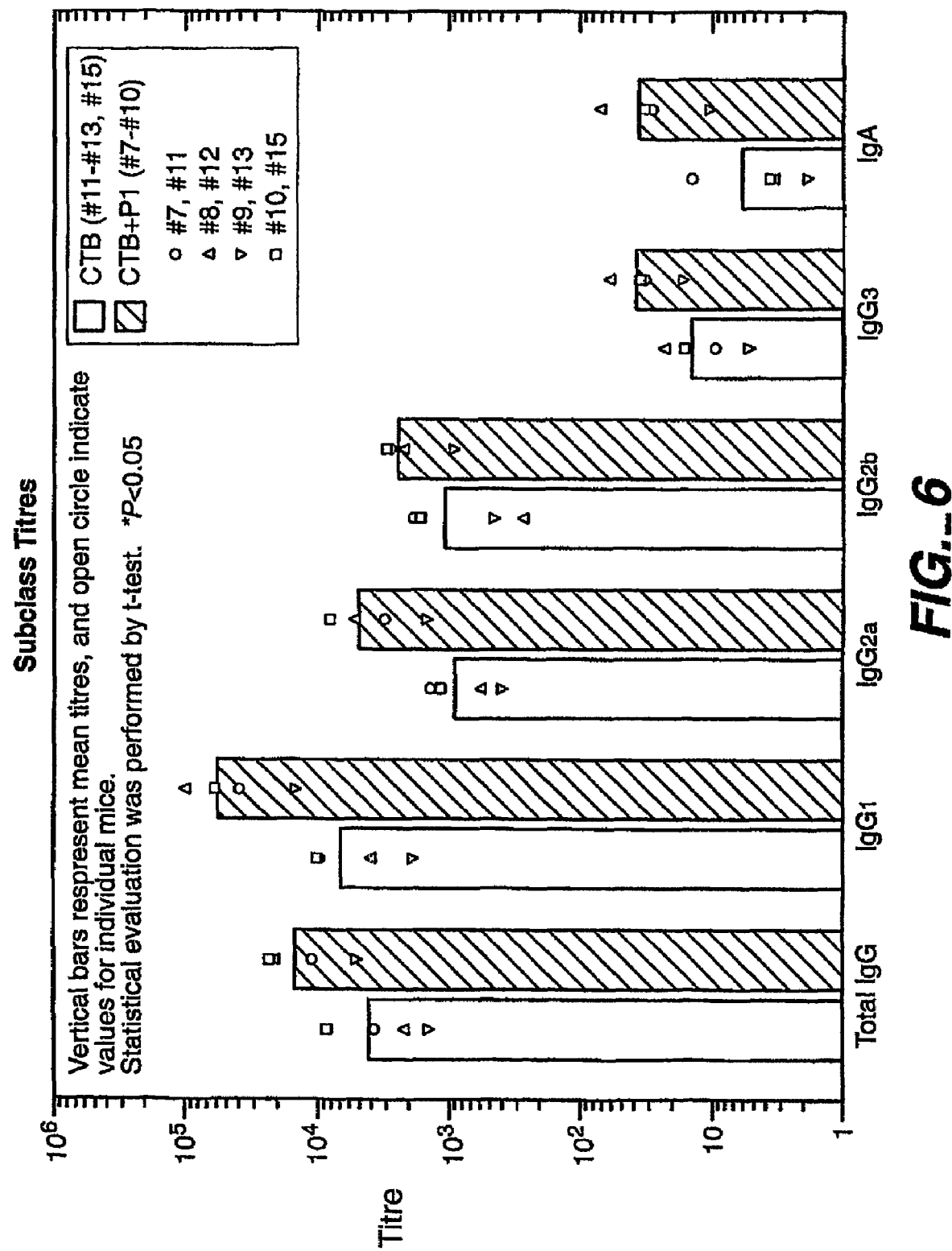
FIG._6

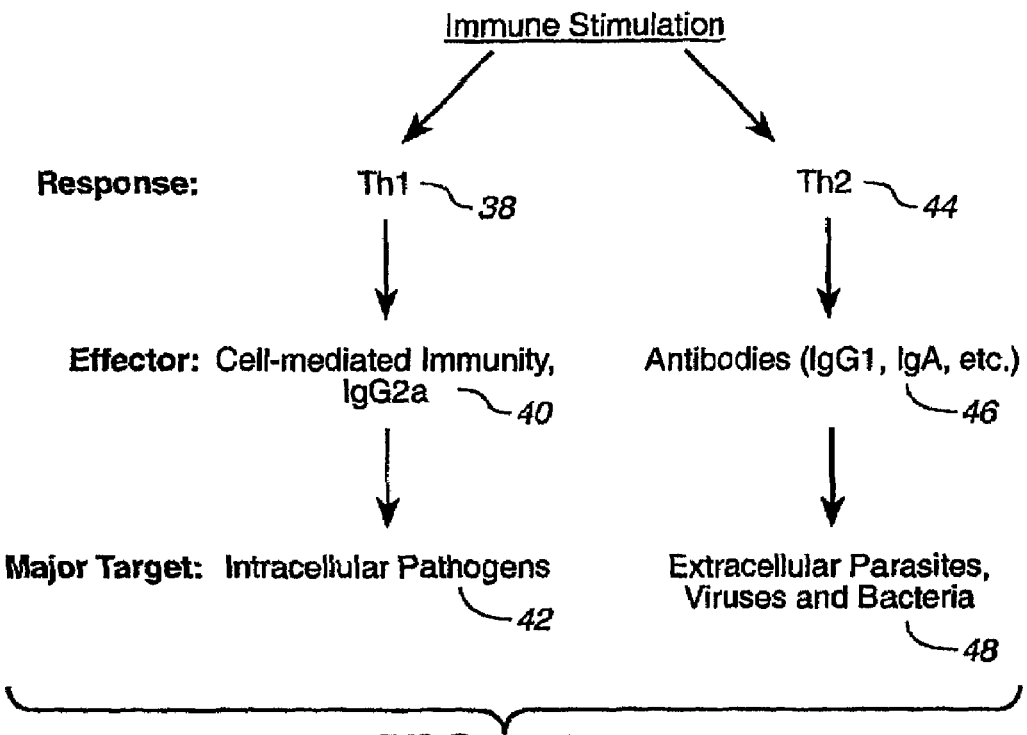
FIG._7
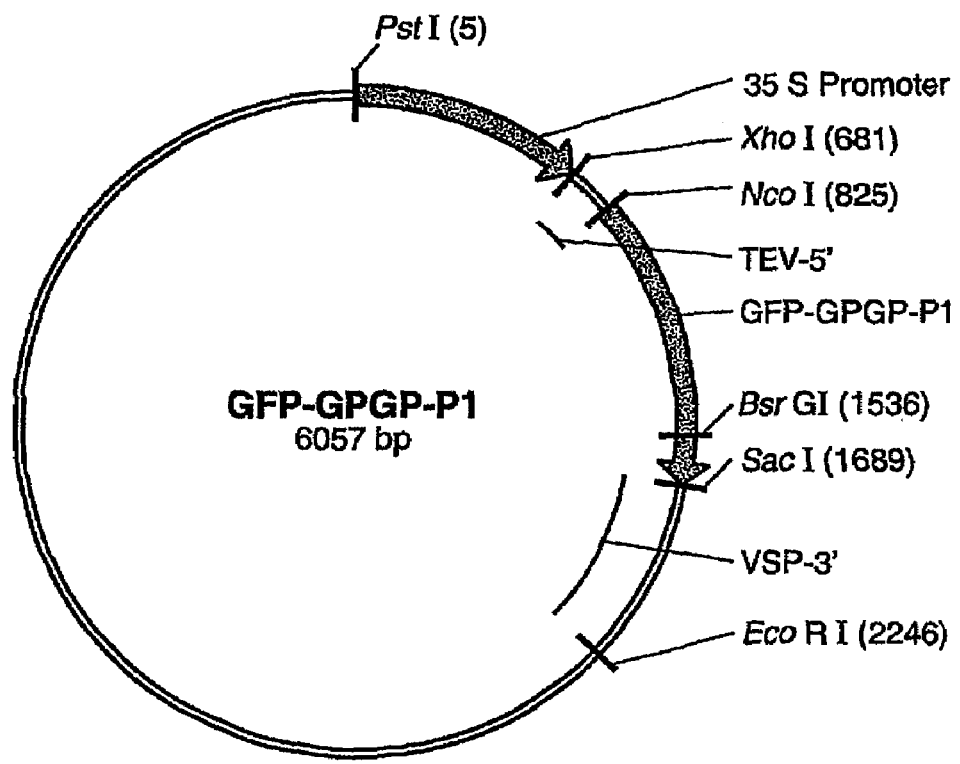
FIG._8

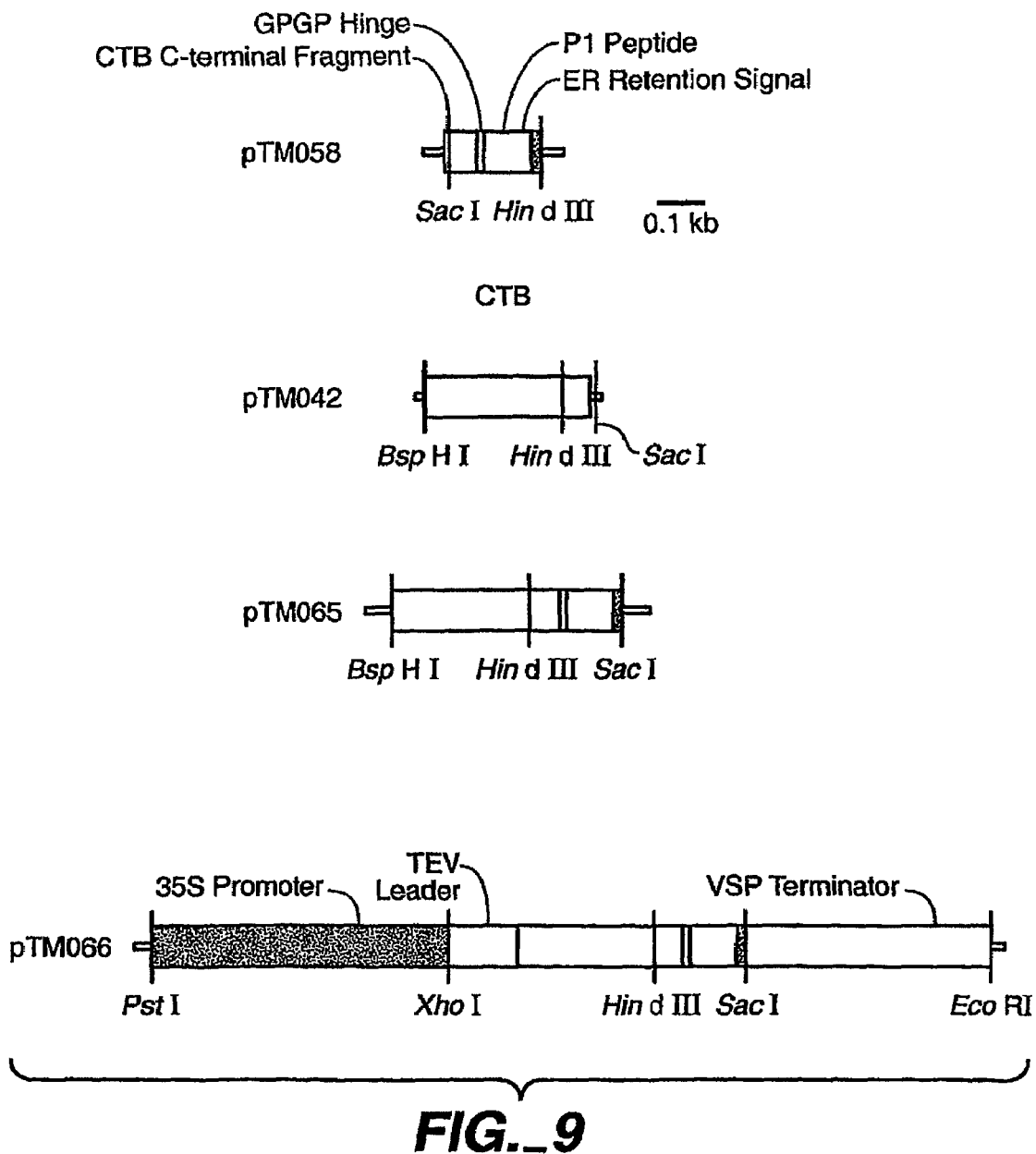
FIG._9

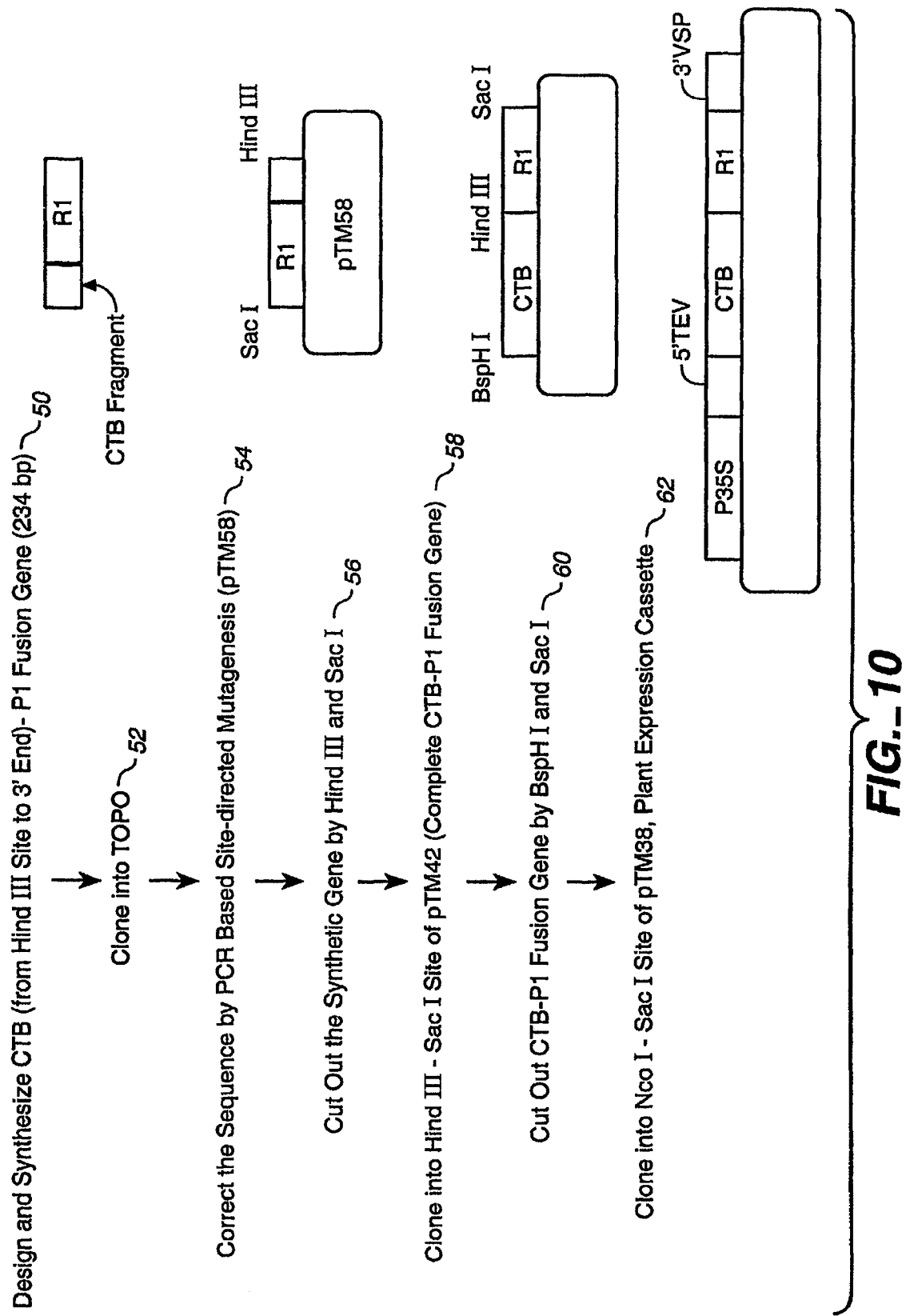
FIG._10

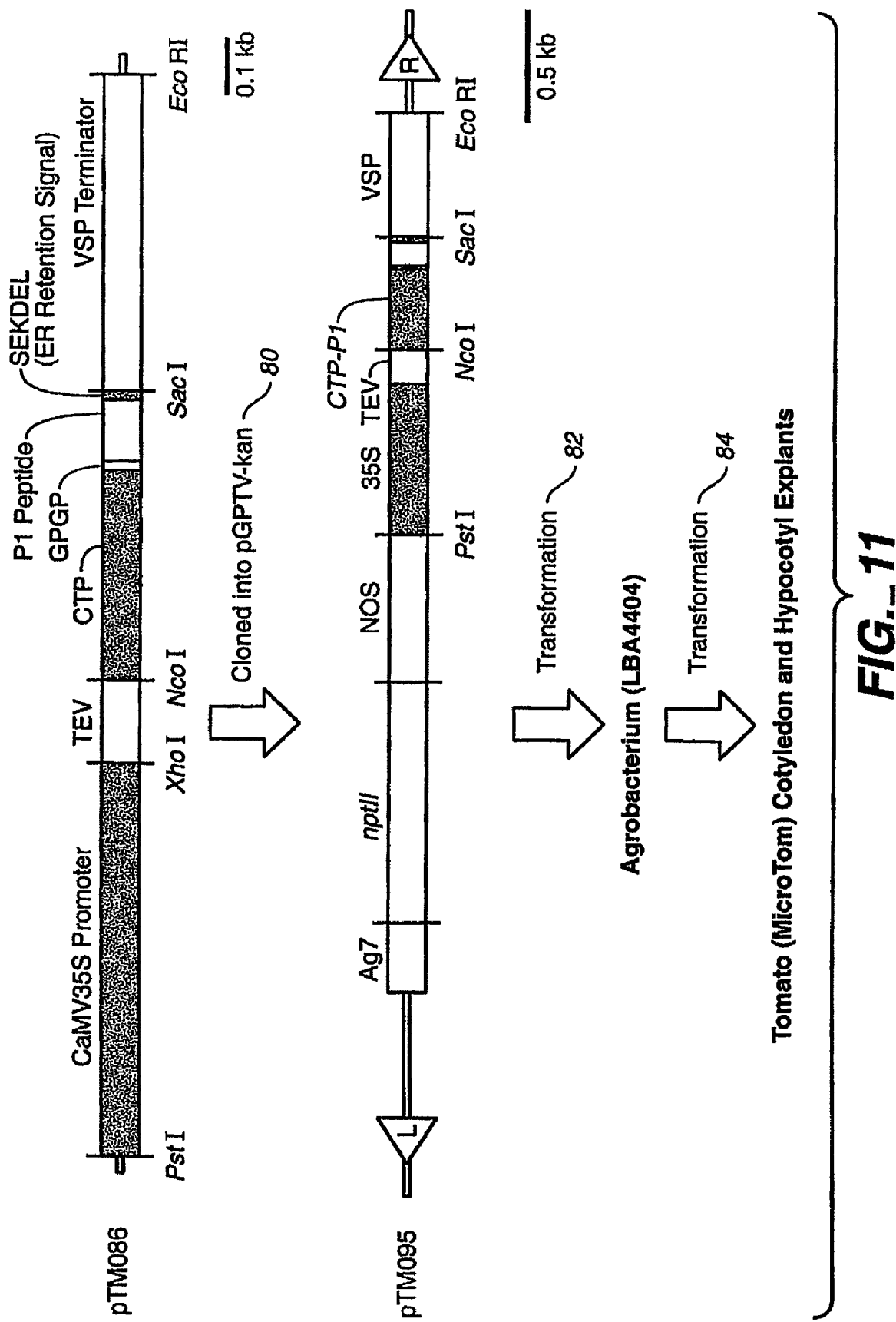
FIG._11

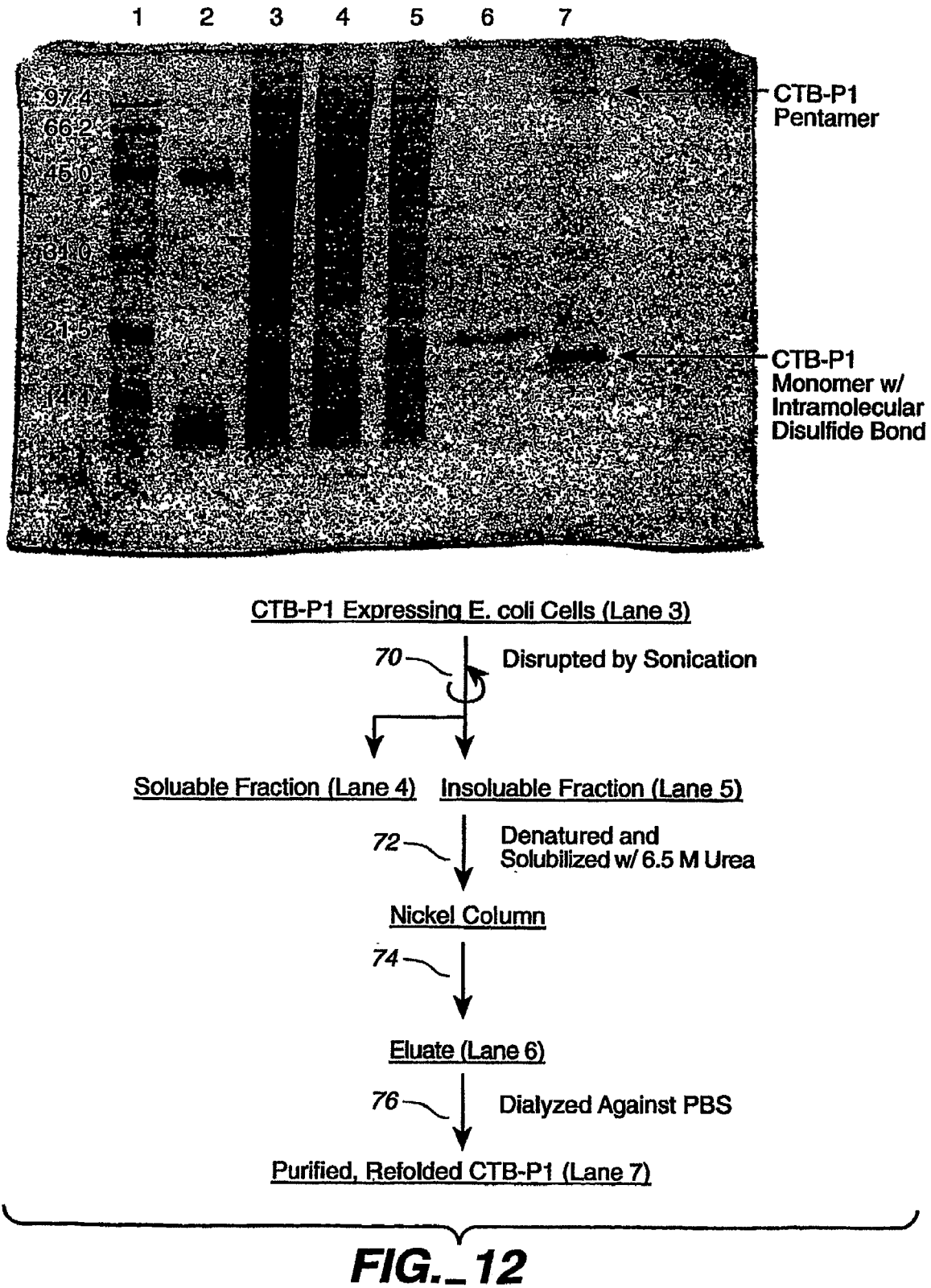
FIG._12

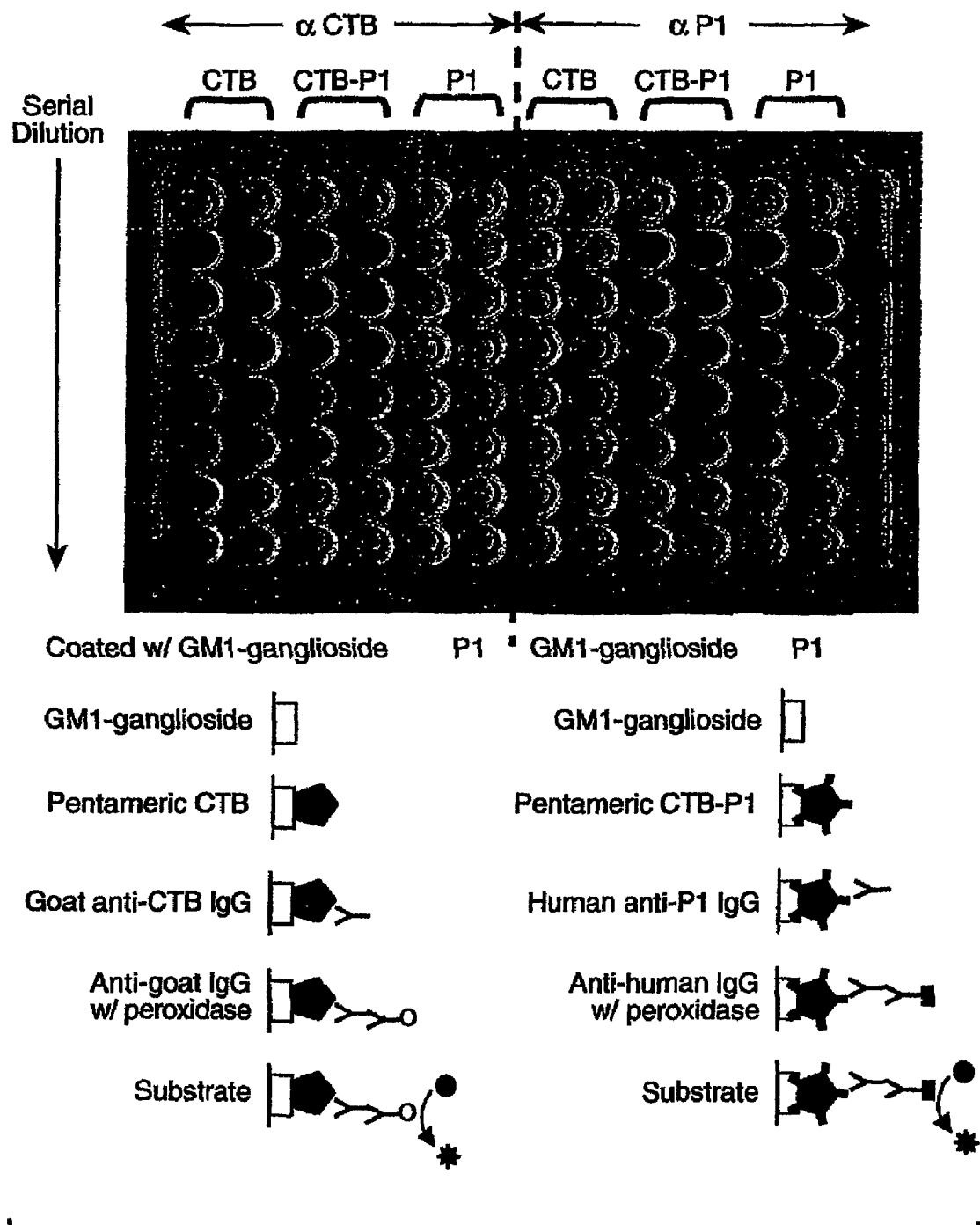
FIG._13

COMPOSITION AND METHOD FOR ENHANCING IMMUNE RESPONSE

CLAIM TO DOMESTIC PRIORITY

This application is a divisional application of application Ser. No. 10/506,796, filed Sep. 3, 2004 now U.S. Pat. No. 7,438,914, which is a U.S. National Stage Application filed under 35 U.S.C. 371 claiming priority from the International Application No. PCT/US03/07073, filed Mar. 6, 2003, which claims the benefit of U.S. Provisional Patent Application Ser. No. 60/362,247, filed Mar. 6, 2002, and which applications are incorporated herein by reference.

FIELD OF THE INVENTION

The present invention relates generally to a composition and method for enhancing immune responses, and more specifically, to a composition and method using HIV-related peptides as an agent to increase immunogenic responses and for delivering fusion proteins to animal cells.

BACKGROUND OF THE INVENTION

Most currently available vaccines consist of killed or live-attenuated pathogens delivered by injection. Despite their success in preventing disease, compelling conceptual, technical and economical reasons exist to seek alternatives to traditional "Jennerian" vaccines.

Vaccines delivered parenterally require injections that must be given by medically trained personnel. Additionally, injection risks possible transmission of infection. Finally, parenteral delivery of vaccines invokes a systemic response, but not a mucosal response.

Subunit vaccines, especially those vaccines that target the mucosal immune system, are viable, safe and effective alternatives. Mucosal vaccines do not require injection; thus, risk of transmission of infection is minimal. Finally, mucosal vaccines elicit immune response both systemically and mucosally.

Additionally, recent breakthroughs suggest that vaccines can be produced in edible tissues of transgenic plants that can then be orally immunogenic. The concept of using transgenic plants as vectors for the production and delivery of edible vaccines has been previously demonstrated.

However, to be effective, mucosal subunit vaccines often need to be co-administered with an "adjuvant." An "adjuvant" is an immunostimulatory agent that would enhance the specific immune responses against the vaccine candidate.

Therefore, a need exists for an immunostimulatory, mucosally-active composition that can be used as a systemic, mucosal, or epidermal adjuvant.

BRIEF DESCRIPTION OF THE DRAWINGS

FIG. 1 depicts the structure of a human immunodeficiency virus (HIV);

FIG. 2 depicts the structure of an adjuvant according to one embodiment;

FIG. 3 illustrates an ELISA determination of anti-CTB antibodies following immunization by gavage;

FIG. 5 illustrates reciprocal dilution of serum $IgG_1$.

FIG. 6 illustrates subclass titers of total serum IgG, $IgG_1$, $IgG_{2a}$, $IgG_{2b}$, $IgG_3$ and IgA.

FIG. 7 is a flowchart illustrating immune response of Th1 and Th2.

FIG. 8 depicts the synthesis of a plant-expression optimized DNA molecule encoding for the P1 peptide;

FIG. 9 depicts maps of plasmids comprised of DNA sequences of CTB, P1, CTB-P1 fusion, and for the plant-expression of the CTB-P1 fusion;

FIG. 10 is a flowchart illustrating the construction of a CTB-P1 fusion protein for plant-expression;

FIG. 11 depicts maps of plasmids for expression of CTB-P1 fusion protein and CTB in tomato;

FIG. 12 shows the expression of CTB-P1 fusion protein in *E. Coli* cells; and FIG. 13 illustrates an ELISA detection of anti-CTB and anti-P1 in *E. Coli* cells.

SUMMARY OF THE INVENTION

Figure 4:
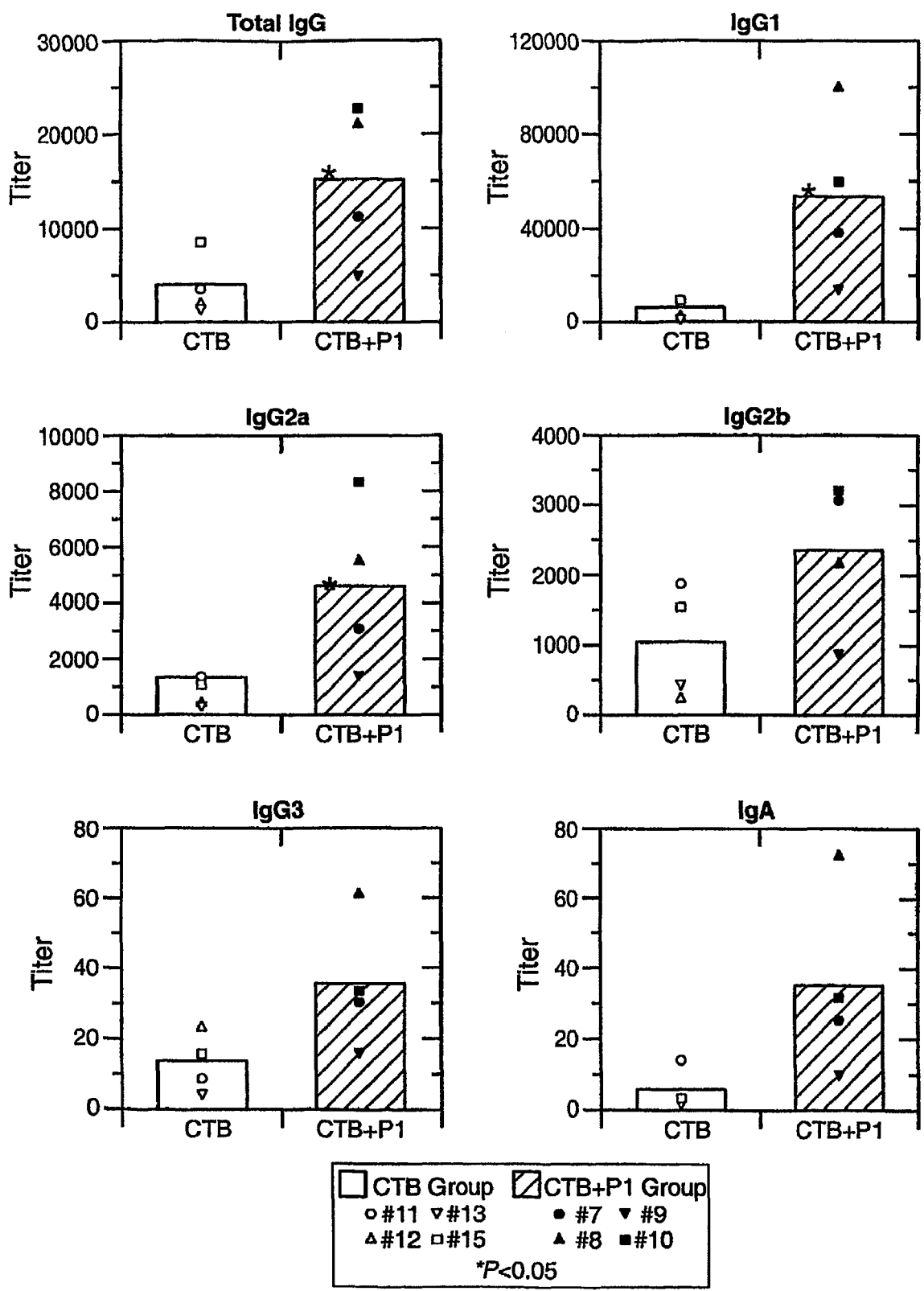
FIG. 4 shows end point titers of anti-CTB antibodies.

The present invention provides a composition and method for enhancing immune response in living organisms, for example, in humans. In one embodiment, and by way of example only, the composition includes, a peptide that when administered to a living organism, enhances the organism's immune response. The composition may also include an antigen, for example, a cholera toxin. The composition may further include the peptide and the antigen together as a fusion protein. The adjuvant peptide may function as a systemic, mucosal or epidermal adjuvant.

In another exemplary embodiment, the adjuvant peptide may be encoded by a genetically-modified living cell. The genetically-modified living cell may also encode an antigen. The peptide and antigen may also be encoded as a fusion protein.

Other independent features and advantages of the method for decreasing nicotine use in living organisms will become apparent from the following detailed description, taken in conjunction with the accompanying drawings which illustrate, by way of example, the principles of the invention.

DETAILED DESCRIPTION OF VARIOUS EMBODIMENTS

This description discloses a composition and method for enhancing immune response in living organisms by administering an oral, mucosal or epidermal adjuvant comprised of one or more HIV-related peptides.

FIG. 1 depicts the structure of an HIV retrovirus. HIV retrovirus 10 is an enveloped retrovirus. HIV retrovirus 10 is comprised of a viral membrane 12, ampiphilic regions 14, charged helices 16, calcium (Ca2+) binding sites 18, gp41 subunits 20, and gp120 subunits 22. Adjuvant peptide 24 facilitates HIV transcytosis across mucosal barriers toward the serosal environment by binding to galactosyl ceramide (GalCer) on the surface of mucosal epithelial cells.

Adjuvant peptide 24 comprises 36 amino acids (SEQ. ID. NO: 1) corresponds to a portion of the gp41 envelope. This peptide includes a conserved epitope (SEQ. ID. NO: 2), which is recognized by the neutralizing human IgG 2F5 and secretory IgAs that functionally neutralize HIV transcytosis through epithelial cells. The conserved aromatic residues are important for GalCer binding.

FIG. 2 depicts the structure of an adjuvant 30 according to one embodiment. Adjuvant 30 comprises peptides 32, linkers 34, and cargo proteins 36. However, alternate embodiments envision adjuvant 30 comprising at least peptides 32, but not necessarily linkers 34 and cargo proteins 36. Peptides 32 may comprise adjuvant peptides as one or more portions of P1 peptides, P5 peptides, or their functional equivalents. In one embodiment, cargo protein 36 is an antigen, for example cholera toxin. In an alternate embodiment, cargo protein 36 is any protein to be delivered to an animal cell.

According to one embodiment, an adjuvant peptide is a portion of the P1 peptide, HIV envelope protein gp41, which includes the conserved epitope, lectin binding site (SEQ. ID. NO: 2). According to an alternate embodiment, the adjuvant peptide is a portion of the P5 peptide, HIV envelope protein gp41 which includes the P1 peptide and a calcium binding site (residue number 622-684). P1 and P5 peptides also include their functional equivalents.

Functional equivalents of adjuvant peptides include peptides or portions of larger proteins with overall sequence or structural similarity to P1 or P5 peptides, and their derivatives, which allow the functionality disclosed here, including, but not limited to, one or more of the following: enhancing the immune response, GalCer binding, binding to the surface of cells containing GalCer, endocytosis to such cells or transcytosis across a tight cell barrier.

Examples of functional equivalents include portions of variants of gp41 in naturally occurring strains of HIV or in laboratory-derived strains of HIV, including, but not limited to, site-directed mutated versions of the gp41 portion of the molecule. Specific, non-limiting, examples of functional equivalents are HIV-1 isolate MN clone V5 (SEQ. ID. NO: 4), HIV-1 isolate 593 clone (SEQ. ID. NO: 5), HIV-1 isolate 98BRRS012 (SEQ. ID. NO: 6), and HIV-1 isolate 19242v3.20 (SEQ. ID. NO: 7).

Adjuvant 30 is capable of mucosal administration. Mucosal administration includes oral, nasal, vaginal, or rectal administration. Adjuvant 30 is also capable of functioning as a systemic, mucosal, or epidermal adjuvant.

Example 1

Example 1 demonstrates that adjuvant peptide enhances immune responses against cholera toxin B subunit by mucosal co-administration of adjuvant peptide and cholera toxin B subunit. Synthetic adjuvant peptide (SEQ. ID. NO: 3) with a C-terminal CONH2, was synthesized by Eurogentec (Belgium) and by the Protein Chemistry Laboratory at Arizona State University. A cysteine residue was added to the beginning of SEQ. ID. NO: 1 to allow for dimerization (residue 649). Cholera Toxin B (CTB) subunit was chosen for co-administration because it is non-toxic and it is a strong mucosal adjuvant. Additionally, CTB binds to GM1 ganglioside whereby being able to target the fused antigen to mucosa.

Synthetic adjuvant peptide 30 micrograms (μg), adjuvant peptide plus Cholera-Toxin B subunit (CTB) (30 and 70 μg, respectively), and CTB (70 μg) were given orally to CD1 female mice (6-7 weeks old) by a gastric feeding tube on day one, eight, and fifteen. The serum, fecal pellets and vaginal secretions were collected prior to and on the second, third and fourth weeks after the first administration. Levels of anti-adjuvant peptide and anti-CTB antibodies were determined by ELISA in each sample.

FIG. 3 illustrates an ELISA determination of anti-CTB antibodies following immunization by gavage of CTB (70 μg), CTB+P1 (70 μg and 30 μg, respectively) or P1 (30 μg). Mice were gavaged on days indicated by arrows and samples of serum (A), fecal (B), and vaginal (C) secretions were collected when indicated. Serum (A) detected systematic levels. Fecal (B) and vaginal (C) both detected mucosal levels.

Samples were serially diluted in phosphate buffered saline containing 0.05% Tween-20 (PBST) containing 1% nonfat dry milk. Plates were coated with CTB overnight at 4° C., blocked with PBST containing 5% nonfat dry milk and then incubated with samples. Antibodies were detected by horseradish peroxidase-conjugated secondary antiisotypic antisera against the appropriate mouse antibodies (rabbit anti-mouse total IgG from CalBiochem, and the following anti mouse antisera: Anti-IgGi, anti-IgG2a, anti-IgG2b, anti-IgG3 from Santa Cruz Biotechnology; and anti-IgA from Sigma. FIGS. 3A-3C show maximal dilutions that allowed quantification.

FIG. 4 illustrates the end point of anti-CTB antibodies four weeks after immunization. Chemiluminescent ELISA was conducted as described in FIG. 3. Titers in FIG. 4 are defined as reciprocals of the highest dilution giving a positive A490 reading above 0.1. FIG. 5 illustrates, for example, reciprocal dilution of serum IgGi. FIG. 6 illustrates subclass titers of total IgG, IgG1, IgG2a, IgG2b, IgG3 and IgA.

While in FIG. 4 antibody titers were below detection levels, co-administration of P1 and CTB to mice resulted in significantly higher titers of anti-CTB antibodies as compared to mice that were given CTB alone. Specifically, in FIG. 3, the level of fecal and vaginal anti-CTB IgA in the second and third week and serum anti-CTB in the second, third and fourth week appeared to be higher in mice fed P1 with CTB than in mice fed only CTB. Moreover, as illustrated in FIG. 6, co-administration of PI with CTB resulted in increasing all serum anti-CTB IgG subclass (IgG1, IgG2a, IgG2b, IgG3) titers by five to ten times in the fourth week, as compared to administration of CTB alone, as shown in FIG. 4.

Therefore, P1 peptide was shown to augment the production of mucosal IgA and serum IgG to co-administered CTB. Because CTB is a strong mucosal immunogen by itself, the increase of both anti-CTB IgG1 and IgG2a levels suggest that the immune enhancement effect of P1 peptide is attributable to activating both Th1 and Th2 response. Th1 and Th2 response is illustrated in FIG. 7. IgG2a 40 effects T1 response 38 through cell-mediated immunity, targeting intracellular pathogens 42. Antibodies 46, such as IgG1 and IgA, effect Th2 response 44 targeting extracellular parasites, viruses and bacteria 48. Secondly, P1 peptide did not induce antibody production against itself, even in the presence of CTB. Therefore, P1 peptide can be used a mucosal adjuvant to enhance immune response in living organisms.

Example 2

In example 2, plasmids were created for the co-expression of adjuvant peptide and GFP in transgenic plants for oral delivery. FIG. 8 depicts the synthesis of a plant-expression optimized DNA molecule encoding for an adjuvant peptide-GFP fusion protein. The sequence coding for adjuvant peptide was inserted behind a DNA spacer encoding a Glycine-Proline-Glycine-Proline (GPGP) hinge. A BsrGI-SacI fragment of this plasmid was cloned in behind a 35 S Promoter. A PstI-EcoRI fragment contains the plant expression cassette. FIG. 8 represents a model delivery system for using fusion proteins to deliver cargo proteins to an animal cell.

FIG. 9 depicts maps of plasmids comprised of DNA sequences of CTB, P1, CTB-P1 fusion and for the plant-expression of the CTB-P1 fusion protein. A plant-expression optimized DNA molecule encoding for P1 peptide was synthesized. The sequence was inserted behind a portion of the gene encoding the C-terminus of the CTB molecule behind a DNA spacer encoding a Glycine-Proline-Glycine-Proline (GPGP) hinge. An endoplasmic reticulum (ER) retention signal was engineered at the Carboxyl-Terminus. The PCR product was cloned into the cloning vector TOP02.1 (Invitrogen) to create pTM058.

Still referring to FIG. 9, a HindIII-SacI fragment of this plasmid was then cloned into pTM042 to create a gene encoding a Carbosyl-terminus fusion of CTB and the P1 peptide in the plasmid pTM065. A BspHI-SacI fragment of this plasmid was cloned into pIBT210.1 (Haq, et al. 1995) behind a CaMV35S promoter and the 5' UTR of Tobacco Etch Virus and in front of the 3' UTR of the soy bean vspB gene to form pTM066. A PstI-EcoRI fragment containing the plant expression cassette was cloned into the $T_1$ plasmid derivative pGPTV-Kan (Becker, et al. 1992) to form pTM067 (not shown).

FIG. 10 is a flowchart illustrating the steps involved in creating a CTB-P1 fusion protein. In step 50, CTB (from HindIII site to the 3' end)-P1 fusion gene is designed and synthesized, a length of 234 base pairs (bp) (SEQ. ID. NO: 8). Next, in step 52, the CTB-P1 fusion gene is cloned into TOPO.

In step 54, the sequence is corrected by PCR-based site-directed mutagenesis to form pTM58 (pTM058). In step 56, the synthetic gene is cut out by HindIII and Sac I. Then in step 58, the synthetic gene is cloned into HindIII-SacI site of pTM42 (pTM042). This represents the complete CTB-P1 fusion gene.

The CTB-P1 fusion gene is then cut out by BspHI and SacI in step 60. Finally, in step 62, the cut out CTB-P1 fusion gene is cloned into the NcoI-SacI site of pTM38. Thus, step 62 clones the CTB-P1 fusion gene into the plant expression cassette. The CTB-P1 fusion gene encodes the CTB-P1 fusion protein (SEQ. ID. NO: 9).

FIG. 11 illustrates an example for a construct for a potentiated edible vaccine. In step 80, pTM086 containing the CTB-P1 fusion gene and the plant expression cassette was cloned into the $T_1$ plasmid derivative pGPTV-Kan (Becker, et al. 1992). The plasmid is then transformed into *Agrobacterium* (LBA4404) in step 82. Finally, in step 84, the *Agrobacterium* is transformed into a tomato, for example MicroTom, cotyledon and hypocotyl explants.

In this example, the target organism for the adjuvant includes, but is not limited to, *Vibrio cholerae*, enterotoxigenic *Escherchia coli*. Other examples would include virus-like particles, for example, Norwalk virus capsid, and antigenic determinants of other pathogens, for example, bacterial, viral or parasitic.

Example 3

The flowchart in FIG. 12 depicts purification protocol of CTB-P1 fusion protein produced in *E. coli*. Resultant fractions from this protocol were resolved by SDS PAGE on the right panel. The following were placed in the first three lanes: Lane 1: molecular weight standards; Lane 2: a mixture of denatured (lower monomeric band) and non-denatured commercially available CT-B (pentameric upper band); Lane 3: whole cell extract from an IPTG-induced *E. coli.*

Following sonication and centrifugations, in step 70, extracts are separated into soluble (Lane 4) and insoluble (lane 5) fraction. The insoluble fraction, in step 72, is solubilized in 6.5 M urea and affinity purification on nickel column in step 74. The eluate (Lane 6) is more than 90% pure and can be subjected to dialysis promoting the refolding and oligomerization of the monomeric CTB-P1 fusion protein. By its mobility we conclude that the fusion protein can assemble into pentamers.

Finally, Eluate was dialyzed against PBS in step 76, and the purified, refolded CTB-P1 is shown in Lane 7. As noted in Lane 7, a CTB-P1 pentameter was produced. Additionally, a CTB-P1 monomer with an intramolecular disulfide bond was also produced.

FIG. 13 demonstrates that the pentameric nature of the fusion protein allows it to bind to $G_{M1}$ gangliosides. The ELISA plate was coated with GM1-ganglioside. On the left half of the plate, anti-CTB was used for detection. On the left half of the plate, anti-P1 was used for detection. CTB, CTB-P1 and P1 samples were applied to the plate as shown. The CTB is commercially available preparation of CTB and P1. CTB-P1 and P1 synthetic peptide are refolded samples purified as explained in FIG. 12. Anti-CTB and anti-P1 are CTB- and P1-specific antibodies, respectively. These results demonstrate that the fusion is both able to retain its pentameric structure as well as its P1 epitope.

Various embodiments of the invention are described above in the Drawings and Description of Various Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A method for delivering a cargo protein to an animal cell, comprising: providing a fusion protein comprising a heterologous cargo protein linked to an isolated peptide consisting of an amino acid sequence selected from SEQ ID NO: 1, SEQ ID NO: 3, SEQ ID NO: 4, SEQ ID NO: 5, SEQ ID NO: 6, or SEQ ID NO: 7; and administering the fusion protein to the animal.

2. The method of claim 1, wherein the cargo protein is an antigen.

3. The method of claim 2, wherein the fusion protein presents the antigen to the immune system of the animal.

4. The method of claim 2, wherein the antigen is a cholera toxin.

5. The method of claim 1, wherein the fusion protein is encoded by a DNA sequence capable of being incorporated into a viral DNA vector.

* * * * *

SEQUENCE LISTING

<160> NUMBER OF SEQ ID NOS: 9

<210> SEQ ID NO 1
<211> LENGTH: 35
<212> TYPE: PRT
<213> ORGANISM: Human immunodeficiency virus type 1
<220> FEATURE:
<221> NAME/KEY: PEPTIDE
<222> LOCATION: (1)..(35)
<223> OTHER INFORMATION: HIV-1 gp41 peptide portion (residues 650-685)

<400> SEQUENCE: 1

Ser Gln Thr Gln Gln Glu Lys Asn Glu Gln Glu Leu Leu Glu Leu Asp
1               5                   10                  15

Lys Trp Ala Ser Leu Trp Asn Trp Phe Asp Ile Thr Asn Trp Leu Trp
            20                  25                  30

Tyr Ile Lys
        35

<210> SEQ ID NO 2
<211> LENGTH: 6
<212> TYPE: PRT
<213> ORGANISM: Human immunodeficiency virus type 1
<220> FEATURE:
<221> NAME/KEY: PEPTIDE
<222> LOCATION: (1)..(6)
<223> OTHER INFORMATION: HIV-1 gp41 peptide portion (residues 663-668)

<400> SEQUENCE: 2

Glu Leu Asp Lys Trp Ala
1               5

<210> SEQ ID NO 3
<211> LENGTH: 36
<212> TYPE: PRT
<213> ORGANISM: Human immunodeficiency virus type 1

<400> SEQUENCE: 3

Cys Ser Gln Thr Gln Gln Glu Lys Asn Glu Gln Glu Leu Leu Glu Leu
1               5                   10                  15

Asp Lys Trp Ala Ser Leu Trp Asn Trp Phe Asp Ile Thr Asn Trp Leu
            20                  25                  30

Trp Tyr Ile Lys
        35

<210> SEQ ID NO 4
<211> LENGTH: 36
<212> TYPE: PRT
<213> ORGANISM: Human immunodeficiency virus type 1
<220> FEATURE:
<221> NAME/KEY: PEPTIDE
<222> LOCATION: (1)..(35)
<223> OTHER INFORMATION: HIV-1 isolate MN clone v5 (residues 649-685)

<400> SEQUENCE: 4

Ser Gln Thr Gln Gln Glu Lys Asn Glu Gln Glu Leu Leu Gly Leu Asp
1               5                   10                  15

Lys Trp Glu Ser Leu Trp Asn Trp Phe Asp Ile Thr Asn Trp Leu Trp
            20                  25                  30

Tyr Ile Lys Ile
        35

<210> SEQ ID NO 5
<211> LENGTH: 36
<212> TYPE: PRT
<213> ORGANISM: Human immunodeficiency virus type 1
<220> FEATURE:
<221> NAME/KEY: PEPTIDE
<222> LOCATION: (1)..(36)
<223> OTHER INFORMATION: HIV-1 isolate 593 clone (residues 649-685)

<400> SEQUENCE: 5

Ser Gln Asn Gln Gln Glu Lys Asn Glu Gln Glu Leu Leu Glu Leu Asp
1               5                   10                  15

Lys Trp Ala Gly Leu Trp Asn Trp Phe Glu Ile Thr Asn Trp Leu Trp
            20                  25                  30

Tyr Ile Lys Ile
        35

<210> SEQ ID NO 6
<211> LENGTH: 36
<212> TYPE: PRT
<213> ORGANISM: Human immunodeficiency virus type 1
<220> FEATURE:
<221> NAME/KEY: PEPTIDE
<222> LOCATION: (1)..(36)
<223> OTHER INFORMATION: HIV-1 isolate 98BRRS012 (residues 649-685)

<400> SEQUENCE: 6

Ser Gln Asn Gln Gln Glu Lys Asn Glu His Glu Leu Leu Glu Leu Asp
 1               5                  10                  15

Lys Trp Ala Asn Leu Trp Asn Trp Phe Asp Ile Thr Asn Trp Leu Trp
            20                  25                  30

Tyr Ile Lys Ile
        35

<210> SEQ ID NO 7
<211> LENGTH: 36
<212> TYPE: PRT
<213> ORGANISM: Human immunodeficiency virus type 1
<220> FEATURE:
<221> NAME/KEY: PEPTIDE
<222> LOCATION: (1)..(36)
<223> OTHER INFORMATION: HIV-1 isolate 1924v3.20 (residues 649-685)

<400> SEQUENCE: 7

Ser Gln Asn Gln Gln Glu Lys Asn Glu Gln Asp Leu Leu Glu Leu Asp
 1               5                  10                  15

Lys Trp Ala Ser Leu Trp Asn Trp Phe Asp Ile Ser Asn Trp Leu Trp
            20                  25                  30

Tyr Ile Lys Ile
        35

<210> SEQ ID NO 8
<211> LENGTH: 522
<212> TYPE: DNA
<213> ORGANISM: Artificial Sequence
<220> FEATURE:
<223> OTHER INFORMATION: Description of Artificial Sequence; note =
      synthetic construct

<400> SEQUENCE: 8
ccatggctat caagctcaag tttggagtgt tcttcactgt gctccttagc tctgcctatg      60
cacatggcac cccacaaaac atcactgact tgtgtgctga gtaccacaac acccaaatcc     120
acaaccctca atgacaagat ctttagctac accgagagcc ttgctggcaa gagggagatg     180
gctatcatcc cttcaagaat ggtgctacct tccaagtgga ggtgcctgga agccaacaca     240
ttgatagcca aaagaaggcc attgagagga tgaaggacac attaggatag cttacctcac     300
tgaggctaag gtggagaagc tttgtgtgtg aacaacaag actccacatg ctattgctgc     360
cattagcatg gcaaatggtc ctggaccttc ccaaacccaa caagagaaga atgagcaaga     420
gcttttggag ttggacaagt ggcaagcctt tggaattggt ttgacatcac caattggctt     480
tggtatatca agatctctga gaaggatgaa ctctaagagc tc                        522

<210> SEQ ID NO 9
<211> LENGTH: 171

-continued

```
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 9

Met Ala Ile Lys Leu Lys Phe Gly Val Phe Phe Thr Val Leu Leu Ser
  1               5                  10                  15

Ser Ala Trp Ala His Gly Thr Pro Gln Asn Ile Thr Asp Leu Cys Ala
             20                  25                  30

Glu Tyr His Asn Thr Gln Ile His Thr Leu Asn Asp Lys Ile Phe Ser
         35                  40                  45

Tyr Thr Glu Ser Leu Ala Gly Lys Arg Glu Met Ala Ile Ile Thr Phe
     50                  55                  60

Lys Asn Gly Ala Thr Phe Gln Val Glu Val Pro Gly Ser Gln His Ile
 65                  70                  75                  80

Asp Ser Gln Lys Lys Ala Ile Glu Arg Met Lys Asp Thr Leu Arg Ile
                 85                  90                  95

Ala Thr Leu Thr Glu Ala Lys Val Glu Lys Leu Cys Val Trp Asn Asn
            100                 105                 110

Lys Thr Pro His Ala Ile Ala Ala Ile Ser Met Ala Asn Gly Pro Gly
        115                 120                 125

Pro Ser Gln Thr Gln Gln Glu Lys Asn Glu Gln Glu Leu Leu Glu Leu
    130                 135                 140

Asp Lys Trp Ala Ser Leu Trp Asn Trp Phe Asp Ile Thr Asn Trp Leu
145                 150                 155                 160

Trp Tyr Ile Lys Ile Ser Glu Lys Asp Glu Leu
                165                 170
```